US011871954B2

(12) United States Patent
Lee et al.

(10) Patent No.: US 11,871,954 B2
(45) Date of Patent: *Jan. 16, 2024

(54) REUSABLE ULTRASONIC TRANSDUCER AND GENERATOR ASSEMBLIES, SURGICAL INSTRUMENTS INCLUDING THE SAME, AND METHODS OF MANUFACTURING THE SAME

(71) Applicant: Covidien LP, Mansfield, MA (US)

(72) Inventors: Weng-Kai K. Lee, Longmont, CO (US); Michael Clifton, Dacono, CO (US); James R. Fagan, Erie, CO (US); Titus Horton, Lyons, CO (US); Keith W. Malang, Longmont, CO (US); Kenneth E. Netzel, Loveland, CO (US); Daniel Simmons, Broomfield, CO (US); Christopher T. Tschudy, Arvada, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/741,567

(22) Filed: May 11, 2022

(65) Prior Publication Data

US 2022/0265305 A1 Aug. 25, 2022

Related U.S. Application Data

(63) Continuation of application No. 16/577,060, filed on Sep. 20, 2019, now Pat. No. 11,331,115.

(Continued)

(51) Int. Cl.
*A61B 17/32* (2006.01)
*B29C 65/08* (2006.01)
(Continued)

(52) U.S. Cl.
CPC ........... *A61B 17/320068* (2013.01); *A61B 17/320092* (2013.01); *B29C 65/08* (2013.01);
(Continued)

(58) Field of Classification Search
CPC .... A61B 17/320068; A61B 17/320092; A61B 2017/00402; A61B 2017/00477; A61B 2017/320075; A61B 2017/320094
See application file for complete search history.

(56) References Cited

U.S. PATENT DOCUMENTS 5,798,599 A 8/1998 Harwood
5,836,897 A 11/1998 Sakurai et al.
(Continued)

OTHER PUBLICATIONS

European Communication Pursuant to Article 94(3) EPC issued in corresponding European Application No. 19 201 085.8 dated Oct. 24, 2022, 4 pages.

(Continued)

*Primary Examiner* — Ryan J. Severson
(74) *Attorney, Agent, or Firm* — Carter, DeLuca & Farrell LLP

(57) ABSTRACT

An ultrasonic transducer and generator (TAG) assembly of a surgical instrument includes generator components and transducer components. The generator components are disposed within a first cavity cooperatively defined by a body portion and a cover. The generator components are covered in a thermally insulative material. The transducer components are disposed within a second cavity cooperatively defined by a proximal housing and a spinner housing.

20 Claims, 7 Drawing Sheets

Related U.S. Application Data

(60) Provisional application No. 62/740,647, filed on Oct. 3, 2018.

(51) Int. Cl.
  *B29C 70/68* (2006.01)
  *A61B 17/00* (2006.01)
  *B29L 31/00* (2006.01)

(52) U.S. Cl.
  CPC .... *B29C 70/68* (2013.01); *A61B 2017/00402* (2013.01); *A61B 2017/00477* (2013.01); *A61B 2017/00526* (2013.01); *A61B 2017/00734* (2013.01); *A61B 2017/320075* (2017.08); *A61B 2017/320094* (2017.08); *B29L 2031/7546* (2013.01)

(56) References Cited

U.S. PATENT DOCUMENTS

| | | | |
|---|---|---|---|
| 5,873,873 A | 2/1999 | Smith et al. | |
| 5,938,633 A | 8/1999 | Beaupre | |
| 6,491,708 B2 | 12/2002 | Madan et al. | |
| 6,588,277 B2 | 7/2003 | Giordano et al. | |
| 8,754,570 B2 | 6/2014 | Voegele et al. | |
| 9,017,355 B2 | 4/2015 | Smith et al. | |
| 9,943,326 B2 | 4/2018 | Ross | |
| 9,974,587 B2 | 5/2018 | Wang et al. | |
| 10,034,685 B2 | 7/2018 | Boudreaux | |
| 10,086,217 B2 | 10/2018 | Liu et al. | |
| 10,582,944 B2 * | 3/2020 | Netzel | A61B 17/320092 |
| 10,610,253 B2 | 4/2020 | Van Tol | |
| 11,123,094 B2 * | 9/2021 | Ross | A61B 17/295 |
| 11,123,096 B2 | 9/2021 | Van Tol | |
| 11,331,115 B2 | 5/2022 | Lee et al. | |
| 2004/0116952 A1 | 6/2004 | Sakurai et al. | |
| 2009/0143799 A1 | 6/2009 | Smith et al. | |
| 2009/0143805 A1 | 6/2009 | Palmer et al. | |
| 2011/0291526 A1 | 12/2011 | Abramovich et al. | |
| 2015/0148832 A1 | 5/2015 | Boudreaux et al. | |
| 2016/0023021 A1 | 1/2016 | Liu et al. | |
| 2016/0206343 A1 | 7/2016 | Ross et al. | |
| 2016/0361083 A1 | 12/2016 | Van Tol | |
| 2017/0202595 A1 | 7/2017 | Shelton, IV | |
| 2019/0076675 A1 | 3/2019 | Liu | |
| 2019/0175208 A1 | 6/2019 | Ross | |
| 2019/0262028 A1 | 8/2019 | Netzel | |
| 2020/0107852 A1 | 4/2020 | Lee | |
| 2020/0155193 A1 | 5/2020 | Netzel | |
| 2020/0229842 A1 | 7/2020 | Van Tol | |
| 2021/0077141 A1 | 3/2021 | Horton | |
| 2021/0153888 A1 | 5/2021 | Van Tol | |
| 2022/0265305 A1 * | 8/2022 | Lee | B29C 65/08 |

OTHER PUBLICATIONS

European Search Report dated Jan. 2, 2020, corresponding to counterpart European Application No. 19201085.8; 9 pages.
European Office Action dated Mar. 1, 2022, issued in corresponding European Appln. No. 19201085, 7 pages.
European Office Action dated Mar. 1, 2022, issued in corresponding European Application No. 19201085, 7 pages.

* cited by examiner

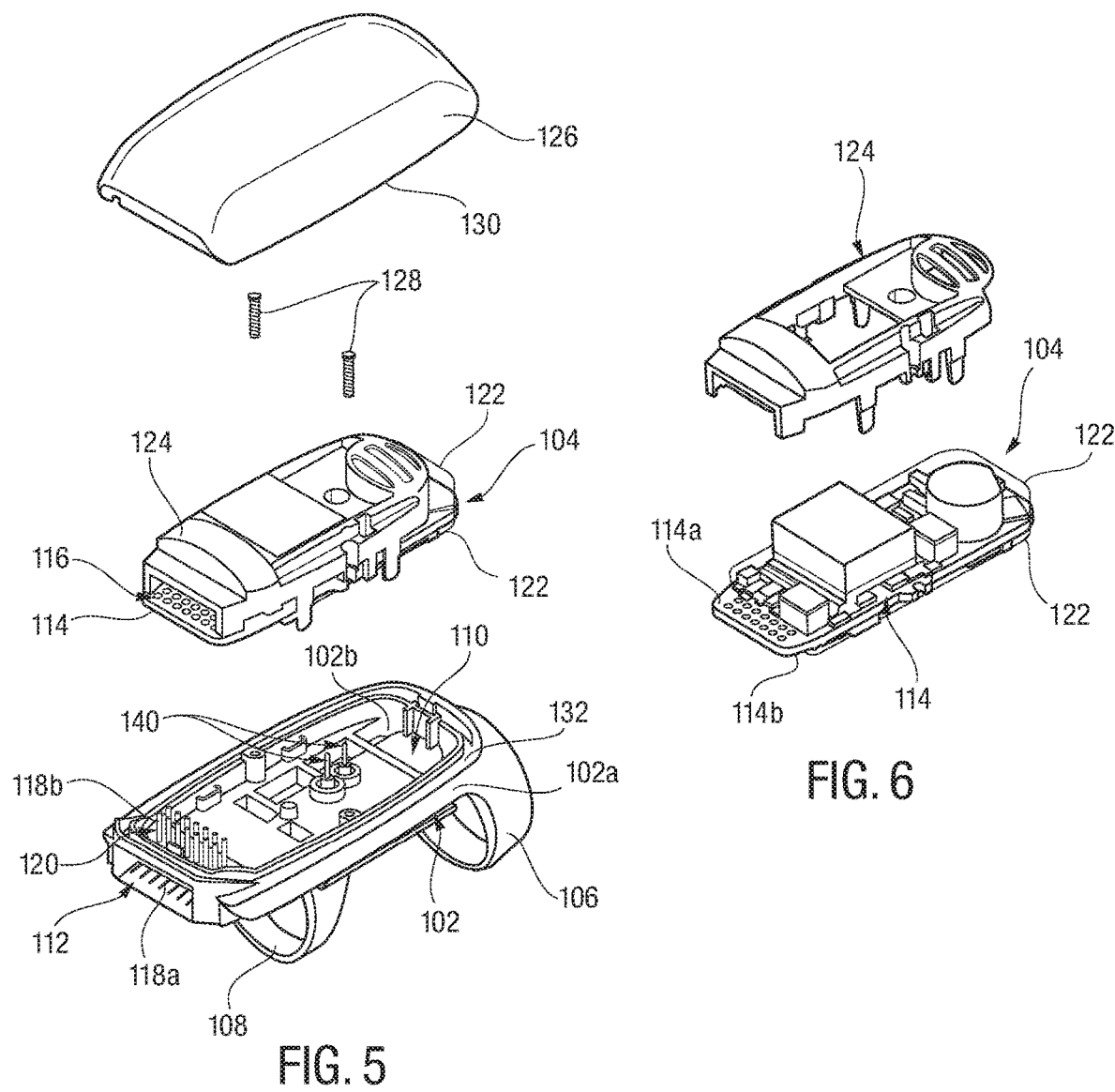

REUSABLE ULTRASONIC TRANSDUCER AND GENERATOR ASSEMBLIES, SURGICAL INSTRUMENTS INCLUDING THE SAME, AND METHODS OF MANUFACTURING THE SAME

CROSS-REFERENCE TO RELATED APPLICATIONS

This application is a continuation application of U.S. patent application Ser. No. 16/577,060 filed on Sep. 20, 2019, which claims the benefit of and priority to U.S. Provisional Patent Application 62/740,647, filed on Oct. 3, 2018, the entire contents of each of which being incorporated by reference herein.

BACKGROUND

Technical Field

The present disclosure relates to surgical instruments and, more particularly, to a reusable ultrasonic transducer and generator assembly of an ultrasonic surgical instrument, an ultrasonic surgical instrument incorporating the same, and methods of manufacturing the same.

Background of Related Art

Some surgical instruments have an end effector configured to apply energy to tissue to treat tissue. An example of such a surgical instrument is an ultrasonic surgical instrument that utilizes ultrasonic energy, i.e., ultrasonic vibrations, to treat tissue. More specifically, a typical ultrasonic surgical instrument utilizes mechanical vibration energy transmitted at ultrasonic frequencies to coagulate, cauterize, fuse, seal, cut, desiccate, fulgurate, or otherwise treat tissue. Such an ultrasonic surgical instrument is configured to transmit ultrasonic energy produced by, for example, a generator and transducer assembly, along a waveguide to an end effector that is spaced-apart from the generator and transducer assembly. The end effector may include a blade and a jaw member configured to clamp tissue against the blade to treat tissue.

Typically, after a use of the ultrasonic surgical instrument, the generator and transducer assembly is sterilized and reused. However, sterilization processes may involve high pressure, extreme heat, and/or moisture that may damage internal components of the generator and transducer assembly.

Accordingly, a need exists for a generator and transducer assembly that can better withstand multiple cycles of various sterilization processes, a surgical instrument including the same, and a method of manufacturing the same.

SUMMARY

In one aspect of the present disclosure, a surgical instrument includes a handle assembly, an elongated body portion extending distally from the handle assembly, a blade extending distally from the elongated body portion, and an ultrasonic transducer and generator ("TAG") assembly for connection to the handle assembly. The TAG assembly is configured to energize the blade member when connected to the handle assembly and includes generator components and transducer components. The generator components are disposed within a first cavity cooperatively defined by a body portion and a cover. A portion of the generator components is covered in a thermally insulative material. The transducer components are disposed within a second cavity cooperatively defined by a proximal housing and a spinner housing. The proximal housing is coupled to the body portion.

In aspects, the thermally insulative material may be a custom conformal coating.

In aspects, the thermally insulative material may be fabricated from a gel or an epoxy.

In aspects, the thermally insulative material may be a silicone gel that covers a top surface of a printed circuit board of the generator components and a bottom surface of the printed circuit board.

In aspects, the thermally insulative material may fill the first cavity.

In aspects, the cover may be ultrasonically welded to an upper portion of the body portion to hermetically seal the generator components in the first cavity.

In aspects, the proximal housing may be ultrasonically welded to the spinner housing to hermetically seal the transducer components within the second cavity.

In aspects, each of the body portion, the cover, the proximal housing, and the spinner housing may be fabricated from a high temperature resistant plastic.

In aspects, the transducer components include a pair of washers, a piezoelectric stack disposed between the pair of washers, and a horn extending distally from the piezoelectric stack. The pair of washers may be fabricated from a material having a similar coefficient of thermal expansion as the piezoelectric stack.

In aspects, the generator components may include an electrical pin connector pre-molded to a pin block and insert-molded into an upper portion of the body portion. A high temperature and moisture resistant sealant may be coated on an interface between the electrical pin connector and the pin block.

In another aspect of the present disclosure, a method of manufacturing a TAG assembly is provided and includes covering a portion of generator components in a thermally insulative material, hermetically sealing the generator components in a first cavity cooperatively defined by a body portion and a cover, and hermetically sealing transducer components within a second cavity cooperatively defined by a proximal housing and a spinner housing.

In some methods, covering the portion of the generator components may include applying a custom conformal coating on the portion of the generator components.

In some methods, covering the portion of the generator components may include filling the first cavity with the thermally insulative material via a hole formed in the cover and sealing the hole in the cover.

In some methods, the cover may be ultrasonically welded to an upper portion of the body portion to hermetically seal the generator components in the first cavity.

Some methods may further include pre-molding an electrical pin connector to a pin block, insert-molding the electrical pin connector into an upper portion of the body portion, and coating the electrical pin connector with a high temperature and moisture resistant sealant.

In yet another aspect of the present disclosure, an ultrasonic transducer and generator (TAG) assembly of an ultrasonic surgical instrument is provided. The TAG assembly includes a body portion, a cover configured to couple to the body portion, and generator components disposed within a first cavity cooperatively defined by the body portion and the cover when the body portion and the cover are coupled to one another. A portion of the generator components is covered in a thermally insulative material. The TAG assembly further includes a proximal housing, a spinner housing configured to couple to the proximal housing, and transducer components disposed within a second cavity cooperatively defined by the proximal housing and the spinner housing when the proximal housing and the spinner housing are coupled to one another. The transducer components include a pair of washers, a piezoelectric stack disposed between the pair of washers, and a horn extending distally from the piezoelectric stack. The pair of washers are fabricated from a material having a similar coefficient of thermal expansion as the piezoelectric stack Further details and aspects of exemplary aspects and features of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The above and other aspects and features of the present disclosure will become more apparent in view of the following detailed description when taken in conjunction with the accompanying drawings, wherein:

FIG. 5 is a perspective view, with parts separated, of generator components of the TAG assembly and a body portion of the TAG assembly of FIG. 1;

FIG. 6 is a perspective view, with parts separated, of the generator components of FIG. 5 and an inner housing;

DETAILED DESCRIPTION

Figure 1:
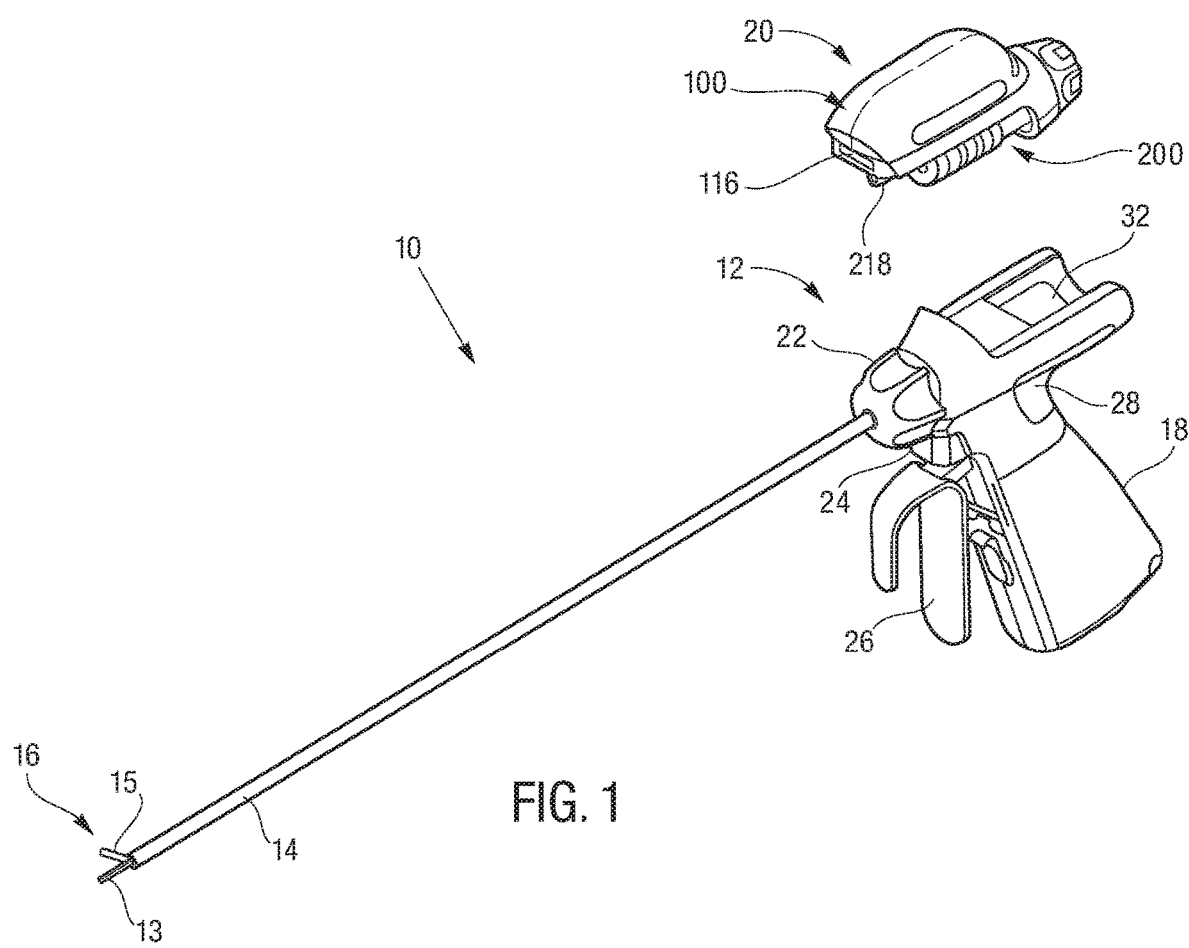
FIG. 1 is a perspective view of an illustrative embodiment of an ultrasonic surgical instrument provided in accordance with the present disclosure, including a TAG assembly thereof disconnected from a handle assembly.

Embodiments of the presently disclosed ultrasonic surgical instruments including transducer and generator ("TAG") assemblies, and methods of manufacturing thereof, are described in detail with reference to the drawings, in which like reference numerals designate identical or corresponding elements in each of the several views. As used herein the term "distal" refers to that portion of the surgical instrument and/or TAG assembly thereof that is closer to the patient, while the term "proximal" refers to that portion of the surgical instrument and/or TAG assembly that is farther from the patient.

The present disclosure is directed to a water-proof, auto-washable and autoclave compatible TAG assembly manufactured to withstand repeated sterilization cycles without being damaged. The generator and transducer components of the TAG assembly are both hermetically sealed within a respective housing, and are coated with thermally insulative material, such as, for example, a silicone gel. A piezoelectric stack of the transducer assembly is surrounded by materials having a similar or the same coefficient of thermal expansion as the piezoelectric stack to prevent cracking of the piezoelectric stack.

Figure 2:
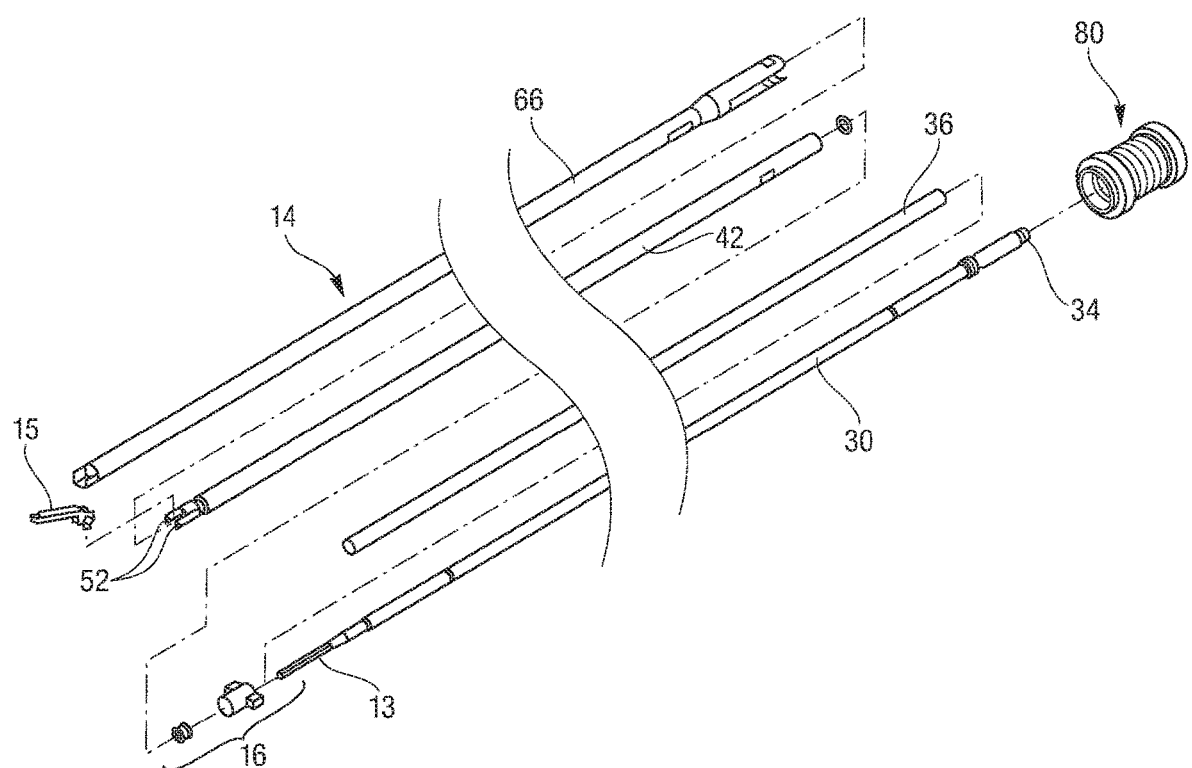
FIG. 2 is an exploded, perspective view of a shaft, a waveguide, and a tool assembly of the ultrasonic surgical instrument of FIG. 1.
Figure 3:
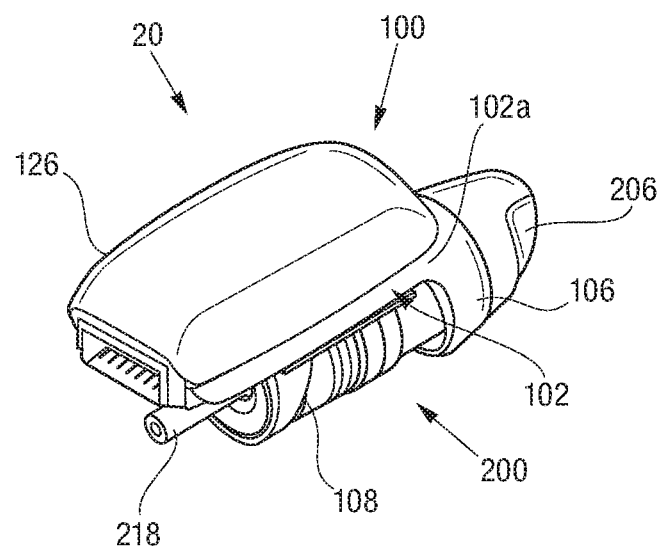
FIG. 3 is a perspective view of the TAG assembly of FIG. 1.
Figure 4:
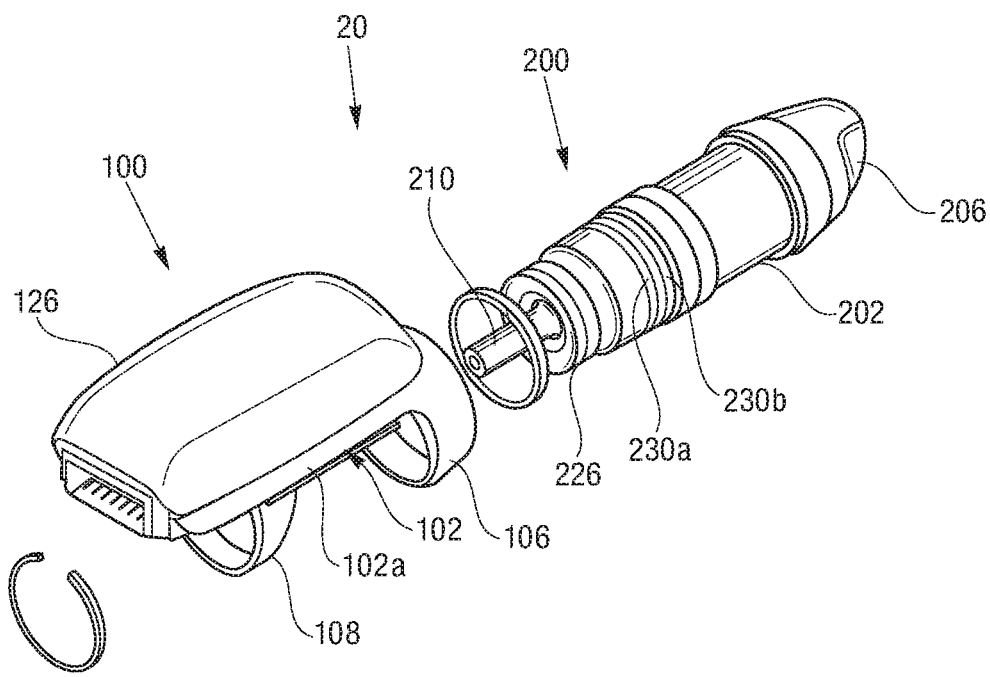
FIG. 4 is a perspective view, with parts separated, of the TAG assembly of FIG. 3.

With reference to FIGS. 1 and 2, an ultrasonic surgical instrument 10 is illustrated and generally includes a handle assembly 12, an elongated body portion 14, and a tool assembly 16. Tool assembly 16 includes a blade 13 and a clamp member or jaw member 15. Handle assembly 12 supports a battery assembly 18 and an ultrasonic transducer and generator assembly ("TAG") 20, and includes a rotatable nozzle 22, an activation button 24, and a clamp trigger 26. Handle assembly 12 includes a body portion 28 defining a recess 32 in a proximal portion thereof dimensioned for releasable receipt of TAG 20 therein. Battery assembly 18 is connected to a lower end of handle assembly 12 to define a fixed handgrip portion of handle assembly 12. Suitable configurations, both cordless and tethered, for providing power and ultrasonic energy, are also contemplated.

Battery assembly 18 and TAG 20 are each releasably secured to handle assembly 12 to facilitate disposal of the entire device, with the exception of battery assembly 18 and TAG 20. However, it is contemplated that any or all of the components of ultrasonic surgical instrument 10 may be configured as disposable single-use components or sterilizable multi-use components. TAG 20 includes a generator assembly 100 and an ultrasonic transducer assembly 200. TAG 20 and its components will be described in further detail below with reference to FIGS. 3-9.

Elongated body portion 14 of ultrasonic surgical instrument 10 includes a waveguide 30, which extends distally from handle assembly 12 to tool assembly 16. A distal portion of the waveguide 30 defines blade 13 of tool assembly 16. A proximal portion of the waveguide 30 is configured to engage TAG 20. Elongated body portion 14 of ultrasonic surgical instrument 10 further includes an isolation tube 36 positioned about waveguide 30 to prevent the transfer of ultrasonic energy from waveguide 30 to an inner support tube 42 of elongated body portion 14. The waveguide 30 and the inner support tube 42 are rotatably coupled to rotatable nozzle 22 such that rotation of nozzle 22 effects corresponding rotation of the inner support tube 42 and the waveguide 30. Elongated body portion 14 further includes an actuator tube 66 coupled to inner support tube 42 and configured to rotate upon rotation of nozzle 22.

Inner support tube 42 of elongated body portion 14 is positioned about isolation tube 36 and includes a distal end having a pair of spaced clamp support arms 52. Spaced clamp support arms 52 are configured to pivotally engage jaw member 15 of tool assembly 16 to enable pivoting of jaw member 15 between an open position, in which jaw member 15 is spaced from blade 13, and a closed position, in which jaw member 15 is approximated relative to blade 13. Jaw member 15 is moved between the open and closed positions in response to actuation of clamp trigger 26.

Outer actuator tube 66 of elongated body portion 14 is slidably supported about inner support tube 42 (although actuator tube 66 may alternatively be slidably disposed within support tube 42) and is operably coupled to jaw member 15 such that jaw member 15 is pivoted from the open position to the closed position as actuator tube 66 is slid about inner support tube 42. Actuator tube 66 is operably coupled with rotatable nozzle 22 such that outer actuator tube 66 is rotatably secured to, and slidable relative to, rotatable nozzle 22. Further, a proximal portion of outer actuator tube 66 is operably coupled with a drive mechanism 80 of handle assembly 12.

Handle assembly 12 includes drive mechanism 80 supported therein for linear movement relative to handle assembly 12. Handle assembly 12 also includes the aforementioned clamp trigger 26, which is operably coupled with drive mechanism 80 such that, in use, when clamping trigger 26 is compressed towards battery assembly 18, outer actuator tube 66 is slid about support tube 42 (in a distal-to-proximal or proximal-to-distal direction) to pivot jaw member 15 from the open position to the closed position in relation to blade 13.

In general, in use, when battery assembly 18 and TAG 20 are attached to handle assembly 12 and waveguide 30, respectively, and ultrasonic surgical instrument 10 is activated, e.g., via actuation of activation button 24, battery assembly 18 provides power to generator assembly 100 of TAG 20, which, in turn, generates an AC signal to drive the ultrasonic transducer assembly 200 of TAG 20. The ultrasonic transducer assembly 200, in turn, converts the AC signal into high frequency mechanical motion. This high frequency mechanical motion produced by the ultrasonic transducer assembly 200 is transmitted to blade 13 via waveguide 30 for application of such ultrasonic energy to tissue adjacent to or clamped between blade 13 and jaw member 15 of tool assembly 16 to treat the tissue.

With reference to FIGS. 3-9, TAG 20 is described. TAG 20 is configured to be received in the recess 32 (FIG. 1) of the handle assembly 12 and generally includes the generator assembly 100, the transducer assembly 200, and a body portion 102 supporting both the generator and transducer assemblies 100, 200. The body portion 102 includes an upper portion 102a supporting generator components 104 of the generator assembly 100. The body portion 102 also has a proximal support member 106 and a distal support member 108 each of which extends beneath the upper portion 102a to define a cradle that rotatably supports the transducer assembly 200.

With reference to FIGS. 5 and 6, the upper portion 102a of the body portion 102 defines a recess 110 therein configured for receipt of the generator components 104 of the generator assembly 100. The generator components 104 include an electrical pin connector 112 and a printed circuit board assembly ("PCBA") 114 each deposited within the recess 110 of the body portion 102. The electrical pin connector 112 may be a 14-pin electrical connector, wherein each of the pins may be right-angle pins that are insert-molded into a bottom portion or floor 102b of the body portion 102. However, other suitable electrical connectors, circuit boards, and/or other components are also contemplated.

The body portion 102 has a distal end defining a port 116 through which a first portion 118a of the electrical pin connector 112 extend. The first portion 118a is configured for receipt in electrical contacts (not explicitly shown) supported on the body portion 28 of the handle assembly 12 to electrically connect the TAG 20 and the smart battery assembly 18 via a connector, e.g., a flex circuit, extending through body portion 28 (see FIG. 1). Once connected, an actuation of the actuation button 24 of the handle assembly 12 will affect a delivery of power from the battery assembly 18 to the generator assembly 100 via the electrical pin connector 112 (see also FIG. 1). A second portion 118b of the electrical pin connector 112 extends upwardly through respective openings defined in the PCBA 114 and a pin block 120 that is disposed toward a distal end of the recess 110 of the body portion 102.

Figure 7:
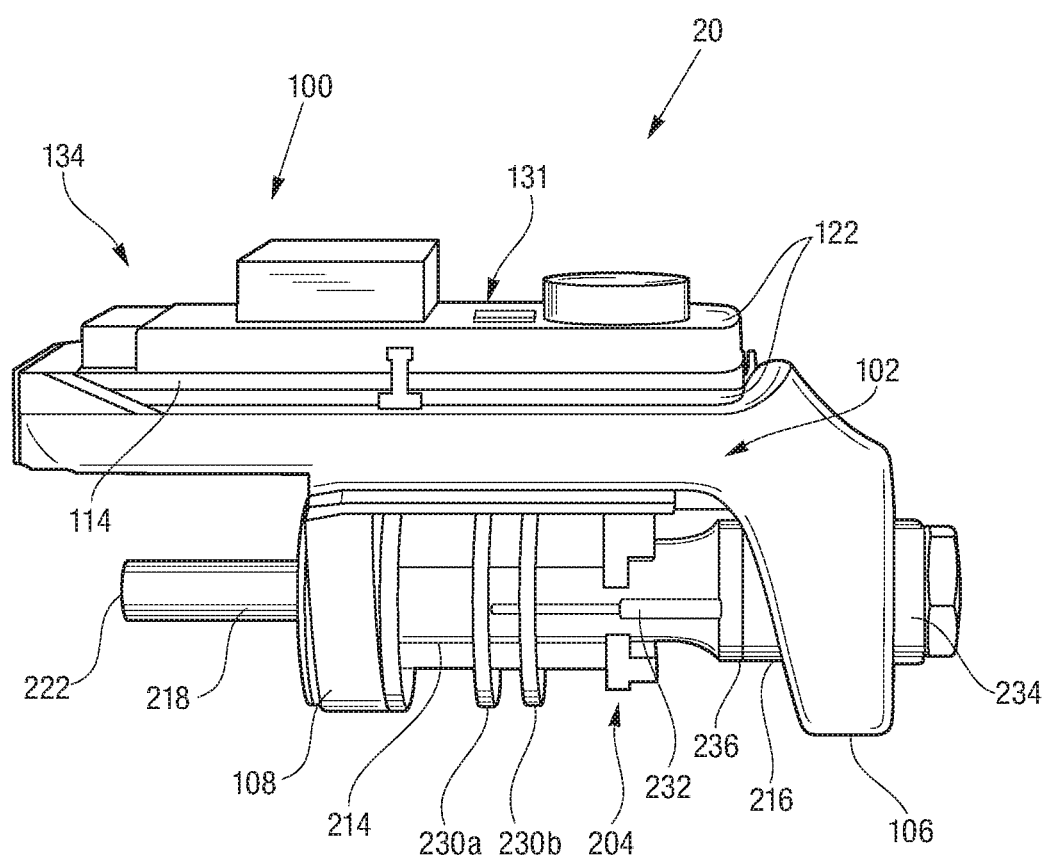
FIG. 7 is a side view, with parts removed or shown transparent, of the TAG assembly of FIG. 1, illustrating the generator and transducer components of the TAG assembly.

With reference to FIGS. 5-7, the PCBA 114 of the generator assembly 100 has an upper surface 114a and a lower surface 114b each covered with the conformal coating 122. The coating 122 is a thermally insulative material, such as, for example, a suitable epoxy or gel, having a thickness from about 0.5 mm to about 8 mm. In embodiments, the thermally insulative material may have a thickness from about 2 mm to about 6 mm. In embodiments, the thermally insulative material may be a silicone gel. The thermally insulative material protects all joints and components of the PCBA 114, and any adjacent components, from the stress of thermal and moisture cycling.

The generator assembly 100 further includes an inner housing 124 and an outer housing or cover 126. The inner housing 124, the outer cover 126, and the body portion 102 may each be fabricated from a high temperature resistant plastic including, but not limited to, polyphenylsulfone, polyaryletherketone, polyether ether ketone, polyetherimide, a liquid-crystal polymer, or any suitable combination thereof. The inner housing 124 couples to lateral portions of the PCBA 114 (e.g., via fasteners 128 or a snap-fit engagement) and partially covers the PCBA 114 and the second portion 118b of the electrical pin connector 112.

The outer cover 126 of the generator assembly 100 has a lower rim 130 configured to be received in a track 132 defined along the outer periphery of the upper portion 102a of the body portion 102. The outer cover 126 and the upper portion 102a of the body portion 102, when coupled, cooperatively define a cavity 134 for receipt of the inner housing 124, the PCBA 114, and the second portion 118b the electrical pin connector 112. As such, upon coupling the outer cover 126 to the upper portion 102a of the body portion 102, the outer cover 126 and the upper portion 102a of the body portion 102 cooperate to encapsulate the inner housing 124, the PCBA 114, and the second portion 118b of the electrical pin connector 112. The lower rim 130 of the outer cover 126 may be coupled to the track 132 of the body portion 102 via ultrasonic welding to hermetically seal the generator components 104 within the cavity 134. In embodiments, the outer cover 126 may be coupled to the body portion 102 via any suitable fastening engagement, whether being permanent or detachable.

During manufacture of the generator assembly 100 of the TAG 20, the electrical pin connector 112 is pre-molded to the pin block 120 and the PCBA 114 using a polymer, such as for example, a liquid-crystal polymer. In embodiments, the electrical pin connector 112 may be pre-molded to the pin block 120 and the PCBA 114 using any suitable adhesive. The upper and lower surfaces 114a, 114b of the PCBA 114 are coated with the thermally insulative material 122 using a conformal coating process, as detailed below. The pin block 120 is insert-molded into the recess 110 of the body portion 102 and then a sealant, such as an epoxy sealant, is sued to seal the molding interface for hermeticity. After applying the conformal coating of the thermally insulative material 122 to the PCBA 114, the now-insulated PCBA 114 and the electrical pin connector 112 are insert-molded into the recess 110 of the body portion 102. A high temperature and moisture resistant sealant, such as, for example, an epoxy, is coated on each of the pins of the electrical pin connector 112 to seal the apertures in the floor 102b of the body portion 102, in the PCBA 114, and in the pin block 120. The sealant prevents the opening of a leak path between the pins and the body portion 102.

With the generator components 104 disposed within the recess 110 of the body portion 102, the outer cover 126 of the generator assembly 100 is positioned over the generator components 104 and the lower rim 130 of the outer cover 126 is inserted into the track 132 of the body portion 102. To fix the outer cover 126 to the body portion 102, an ultrasonic weld is applied to the lower rim 130 of the outer cover 126, thereby hermetically sealing the generator components 104 (e.g., the electrical pin connector 112 and the PCBA 114) in the cavity 134.

In an alternate embodiment, the thermally insulative material 122 may be applied after insertion of the PCBA 114 into the body portion 102 instead of or in addition to being applied prior. For example, after covering the PCBA 114 with the outer cover 126, the thermally insulative material 122 may be injected into the cavity 134 via a hole (not shown) formed in the outer cover 126. The thermally insulative material 122 may be injected until the cavity 134 is substantially filled with the thermally insulative material 122. It is contemplated that the thermally insulative material 122 may fill the entire cavity 134 of the outer cover 126. The hole in the outer cover 126 may then be filled using a sealant (e.g., an epoxy).

With reference to FIGS. 3, 4 and 7-9, the transducer assembly 200 of TAG 20 is described. The transducer assembly 200 extends through the proximal end of the body portion 102 and is rotatably supported on the cradle defined by supports 106, 108. The transducer assembly 200 generally includes a proximal housing 202, a spinner housing 226, and transducer components 204 configured to be received within a cavity cooperatively defined by the proximal housing 202 and the spinner housing 226 when the proximal housing 202 and the spinner housing 226 are coupled to one another. The proximal housing 202 and the spinner housing 226 may be fabricated from a high temperature resistant plastic including, but not limited to, polyphenylsulfone, polyaryletherketone, polyether ether ketone, polyetherimide, a liquid-crystal polymer, or any suitable combination thereof. The proximal housing 202 and the spinner housing 226 may be ultrasonically welded to one another to hermetically seal the transducer components 204 therein, as will be described in greater detail below.

The proximal housing 202 has a torque knob 206 at its proximal end. When the proximal housing 202 is supported on the body portion 102, the torque knob 206 extends from the proximal end of the body portion 102. The torque knob 206 includes an internal surface with a plurality of longitudinal ribs 208 defining longitudinal recesses 210 therebetween. The longitudinal recesses 210 receive corresponding tabs 212 extending proximally from an internal housing 214 positioned about the transducer components 204, whereby rotation of the torque knob 206 causes corresponding rotation of the internal housing 214.

Figure 8:
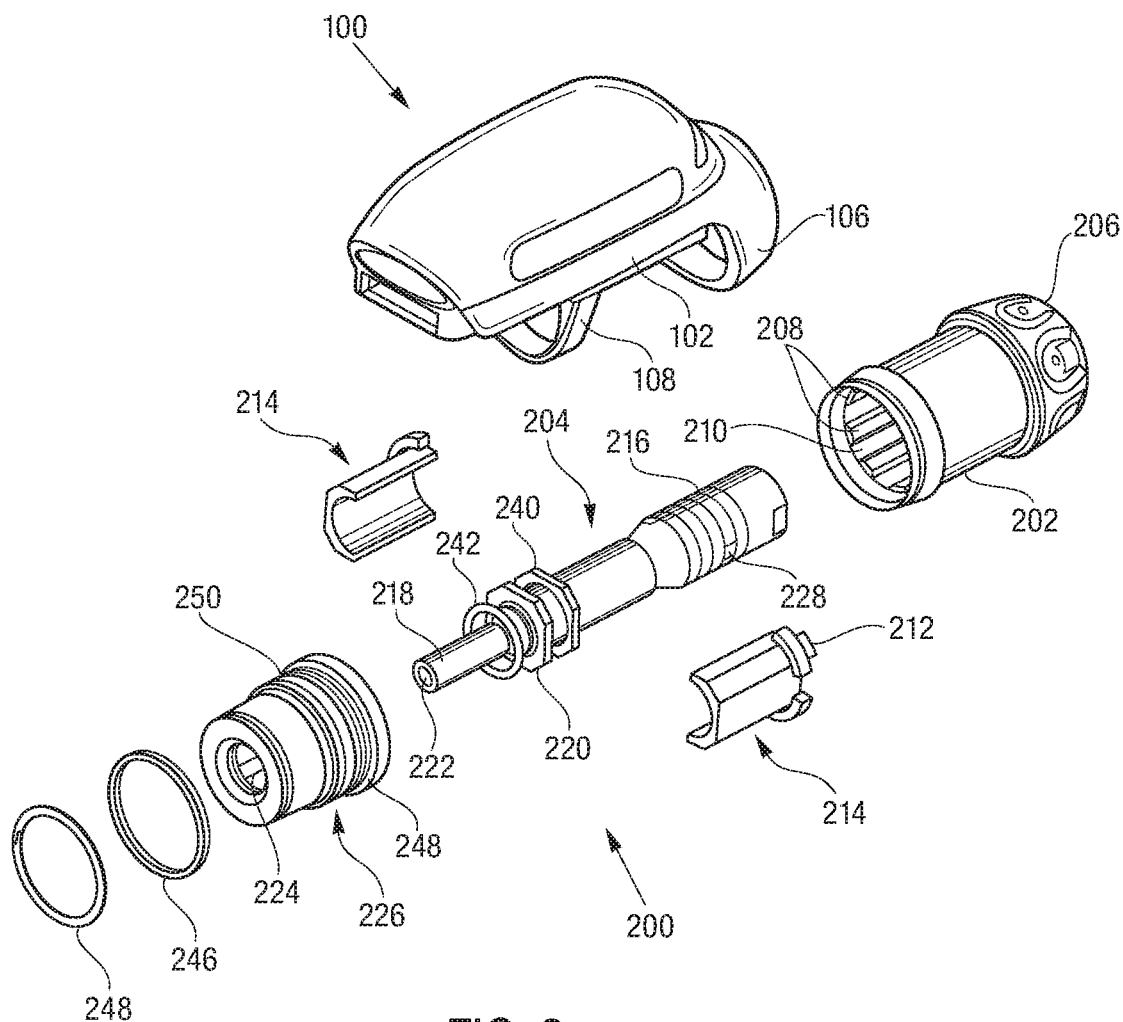
FIG. 8 is a perspective view, with parts separated, of the transducer assembly disconnected from the body portion of the TAG assembly of FIG. 1.
Figure 9:
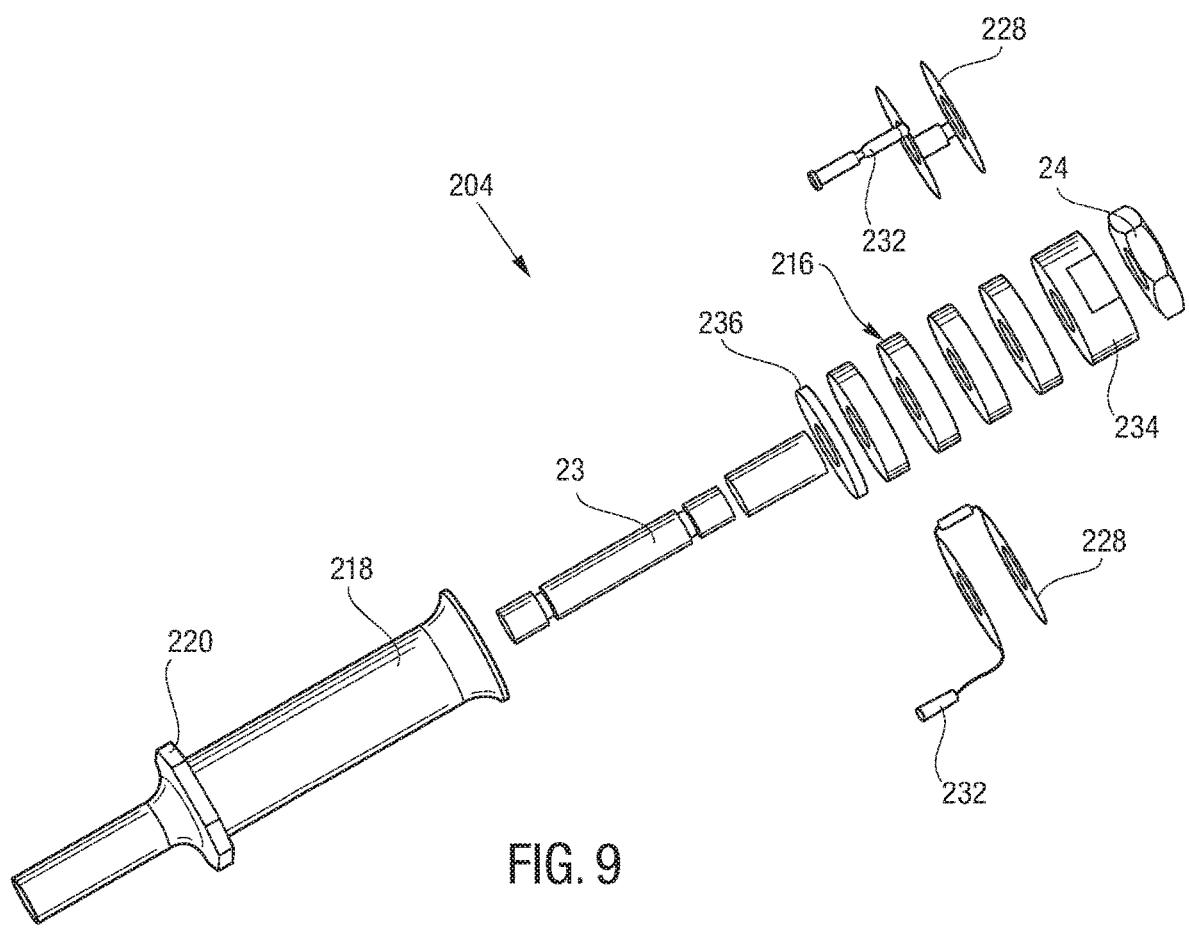
FIG. 9 is a perspective view, with parts separated, of the transducer components of the transducer assembly of FIG. 8.

With reference to FIGS. 7-9, the proximal housing 202 and the spinner housing 226 support the transducer components 204 of the TAG 20, including a piezoelectric stack 216 and a forwardly extending horn 218. Horn 218 has a horn flange 220 secured thereto having a polygonal cross-section. The horn 218 has a threaded bore 222 at its distal end that threadably engages a threaded extension 34 of the waveguide 30 (FIG. 2). The internal housing 214 and the transducer components 204 are positioned within a longitudinal bore 224 extending through the spinner housing 226. The longitudinal bore 224 of the spinner housing 226 has a polygonal cross-sectional configuration corresponding to the outer cross-sectional configuration of the internal housing 214 and the horn flange 220, whereby rotation of the internal housing 214 causes corresponding rotation of the spinner housing 226 and the horn flange 220.

The piezoelectric stack 216 of the transducer components 204 includes first and second electrodes 228 disposed between piezoelectric elements of the piezoelectric stack 216. The electrodes 228 include corresponding first and second electrode extensions 232 extending distally from the piezoelectric stack 216. The piezoelectric stack 216 may include transducer crystals and electrodes 228 that are outer diameter centered rather than inner diameter centered to simplify the assembly of the transducer components 204. The outer diameter centering ensures a concentric arrangement of the transducer crystals and the electrodes 228. The electrodes 228 may have an outer diameter that is larger than the transducer crystals and an inner diameter that is smaller than the transducer crystals to allow for tolerances and ease of assembly. Transducer assembly 200 includes first and second spaced-apart contact rings 230a, 230b disposed annularly about the exterior of the spinner housing 226. The first and second contact rings 230a, 230b are rotatably associated with corresponding contacts 140 of the generator assembly 100 (FIG. 5) that extend through the floor 102b of the body portion 102. A sealant (e.g., an epoxy) may be applied to the contact rings 230a, 230b to seal off the contact rings and the spinner housing 226.

To drive the piezoelectric stack 216, the first and second electrodes 228 are energized by first and second electrical potentials, respectively. In order to supply these first and second potentials to the electrodes 228, the generator components 104 of the TAG 20 provide the first and second electrical potentials to the contacts 140 of the generator assembly 100, which transmit the first and second electrical potentials to the first and second electrodes 228 of the piezoelectric stack 216 via the first and second contact rings 230a, 230b.

The transducer components 204 further include a proximal washer 234 and a distal washer 236 disposed on opposite ends of the piezoelectric stack 216, respectively. The washers 234, 236 may be fabricated from a metal, wherein the proximal washer 234 may be fabricated from martensitic stainless steel and the distal washer 236 may be fabricated from titanium. It is contemplated that the washers 234, 236 may be fabricated from any suitable material having a similar or the same coefficient of thermal expansion as the piezoelectric stack 216. In embodiments, the horn 218 may also have the same or similar coefficient of thermal expansion as the piezoelectric stack 216. By having the same or similar coefficient of thermal expansion as the piezoelectric stack 216, the washers 234, 236 and horn 218 prevent cracks from forming in the piezoelectric stack 216 during thermal cycling. The horn 218 may help guide assembly to prevent scraping of PTFE liner. A stress rod 23 may be fixed to a proximal end of the horn 218 and extend proximally therefrom. A proximal end of the stress rod 23 may be coupled to a nut 24 disposed proximally of the washer 234 or within the washer 234. The nut 24 may be a hexagonal nut and is tightened onto the stress rod 23 to fix the piezoelectric stack 216 in place. The stress rod 23 may screw into the horn 218 and then the nut 24 may be screwed onto the stress rod 23. The stress rod 23 may experience tension during and after the nut 24 is screwed into place.

The transducer components 204 further include a bushing 240 positioned proximally of the horn flange 220, and an O-ring 242 positioned distally of the horn flange 220. The bushing 240 is positioned between a distal surface of the internal housing 214 and a proximal face of the horn flange 220, and functions to support the transducer components 204 while inhibiting the transfer of ultrasonic vibration to the spinner housing 226. The O-ring 242 is positioned between a proximal surface of the spinner housing 226 and a distal face of the horn flange 220, and seals the horn flange 220 to the spinner housing 226 to further inhibit the transfer of ultrasonic vibration to the spinner housing 226.

A bushing 246 (e.g., a TEFLON bushing) is received within a first groove 284 formed in a proximal end of the spinner housing 226. The bushing 246 is positioned distally of the distal support member 108 of the body portion 102 of the TAG 20 in order to inhibit binding of the transducer components 204 during rotation. Additionally, a spiral ring 248 is received within a second grove 250 formed in the proximal end of the spinner housing 226. The spiral ring 248 is positioned distally of the bushing 246 in order to retain the spinner housing 226 within the body portion 102 of the TAG 20.

During manufacture of the transducer assembly 200 of TAG 20, the piezoelectric stack 216 is positioned within the proximal housing 202 and the spinner housing 226. For example, a distal end of the proximal housing 202 may be received in a proximal end of the spinner housing 226, followed by welding of the distal end of the proximal housing 202 to the proximal end of the spinner housing 226. The proximal housing 202 and the spinner housing 226 are ultrasonically welded to one another to hermetically seal the piezoelectric stack 216 and the washers 234, 236 therein. To attach the TAG 20 to the body portion 28 of the handle assembly 12, the transducer assembly 204 is positioned in the circular recess portion 32 (FIG. 1) of the body portion 28 of the handle assembly 12, during which time, the threaded extension 34 (FIG. 2) of the waveguide 30 is received in the threaded bore 222 (FIG. 7) of the horn 218. In order to threadably secure the waveguide 30 to the horn 218, the rotatable nozzle 22 is gripped, and the horn 218 is rotated by rotating the proximal housing 202 via the torque knob 206.

After a use of the ultrasonic surgical instrument 10, the TAG 20 may be detached from the handle assembly 12 and put through a sterilization cycle. Due to above-described construction of the TAG 20, the generator components 104 and the transducer components 204 of the TAG 20 can undergo high heat, high pressure, and/or high moisture sterilization processes without being damaged.

The performance of the piezoelectric stack 216 of the transducer components 204 may be impacted by going through a high temperature process (i.e. an autoclave). As described in U.S. Pat. No. 9,943,326, the entire contents of which being incorporated by reference herein, the performance of the transducer may be calibrated prior to its use and then adjusted based on its usage. The calibration may also employ an algorithm that adjusts the calibration in expectation that the transducer will be put through a high temperature autoclave cycle before it is used. The algorithm may include a reduction in the calibration of the transducer by about 1% to about 5% and, in some embodiments about 2.2%, to counteract the effects of the autoclave.

In embodiments, the transducer may be equipped with a sensor configured to sense the number of times the transducer underwent an autoclave. The calibration of the transducer may be changed based on the number of autoclaves the transducer endured.

The acoustic wave velocity produced by the transducer was found to increase by 15-20% over the first 25-50 autoclave cycles, whereby the performance of the transducer substantially stabilizes after the first 25-50 autoclave cycles. It was found that by baking the transducer at approximately 150° C. for approximately 40 hours, the change in velocity was reduced from about 15-20% to about 2%. Baking the transducer at higher temperatures risks degrading the performance of the transducers, whereas baking the transducer at lower temperatures requires more bake time to get the same effect. Accordingly, prior to use of the piezoelectric stack 216, the piezoelectric stack 216 may be autoclaved at about 140° C. to about 160° C. for about 30 hours to about 50 hours. In this way, the impact of future autoclaves on the piezoelectric stack 216 will be reduced.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic transducer and generator (TAG) assembly configured to energize an ultrasonic blade, the TAG assembly comprising:
   a generator assembly including:
      a body portion;
      a cover configured to attach to the body portion, the body portion and the cover cooperatively defining a first cavity when the cover is attached to the body portion; and
      at least one generator component configured for receipt within the first cavity, wherein the at least one generator component is covered in a thermally insulative material; and
   a transducer assembly including:
      a proximal housing;
      a spinner housing configured to attach to the proximal housing, the proximal housing and the spinner housing cooperatively defining a second cavity when the spinner housing is attached to the proximal housing; and
      at least one transducer component configured for receipt within the second cavity.

2. The TAG assembly according to claim 1, wherein the proximal housing is configured to couple to the body portion.

3. The TAG assembly according to claim 1, wherein the thermally insulative material is a conformal coating.

4. The TAG assembly according to claim 1, wherein the thermally insulative material is fabricated from at least one of a gel or an epoxy.

5. The TAG assembly according to claim 4, wherein the at least one generator component includes a printed circuit board, the thermally insulative material being a silicone gel that covers a top surface of the printed circuit board and a bottom surface of the printed circuit board.

6. The TAG assembly according to claim 1, wherein the thermally insulative material fills the first cavity.

7. The TAG assembly according to claim 1, wherein the cover is ultrasonically welded to an upper portion of the body portion to hermetically seal the at least one generator component within the first cavity.

8. The TAG assembly according to claim 1, wherein the proximal housing is ultrasonically welded to the spinner housing to hermetically seal the at least one transducer component within the second cavity.

9. The TAG assembly according to claim 1, wherein each of the body portion, the cover, the proximal housing, and the spinner housing is fabricated from a high temperature resistant plastic.

10. The TAG assembly according to claim 1, wherein the at least one transducer component includes:
    a pair of washers;
    a piezoelectric stack disposed between the pair of washers; and
    a horn extending distally from the piezoelectric stack.

11. The TAG assembly according to claim 10, wherein the pair of washers are fabricated from a material having a similar coefficient of thermal expansion as the piezoelectric stack.

12. The TAG assembly according to claim 1, wherein the at least one generator component includes an electrical pin connector pre-molded to a pin block and insert-molded into an upper portion of the body portion.

13. The TAG assembly according to claim 12, wherein a high temperature and moisture resistant sealant is coated on an interface between the electrical pin connector and the pin block.

14. A method of manufacturing an ultrasonic transducer and generator (TAG) assembly, the method comprising:
    covering at least one generator component of the TAG assembly within a thermally insulative material;
    hermetically sealing the at least one generator component in a first cavity defined by a generator housing assembly; and
    hermetically sealing at least one transducer component of the TAG assembly within a second cavity defined by a transducer housing assembly.

15. The method according to claim 14, further comprising coupling the generator housing assembly and the transducer housing assembly to one another.

16. The method according to claim 14, wherein covering the at least one generator component includes applying a conformal coating on the at least one generator component.

17. The method according to claim 14, wherein covering the at least one generator component includes:
    filling the first cavity with the thermally insulative material via a hole formed in a cover of the generator housing assembly; and
    sealing the hole in the cover.

18. The method according to claim 14, wherein a cover of the generator housing assembly is ultrasonically welded to an upper portion of a body portion of the generator housing assembly to hermetically seal the at least one generator component within the first cavity.

19. The method according to claim 14, further comprising:
    pre-molding an electrical pin connector to a pin block;
    insert-molding the electrical pin connector into the generator housing assembly; and
    coating the electrical pin connector with a high temperature and moisture resistant sealant.

20. The method according to claim 14, wherein the at least one transducer component includes:
    a pair of washers;
    a piezoelectric stack disposed between the pair of washers; and
    a horn extending distally from the piezoelectric stack, the pair of washers being fabricated from a material having a similar coefficient of thermal expansion as the piezoelectric stack.

* * * * *